United States Patent [19]

Leuba et al.

[11] Patent Number: 5,057,542
[45] Date of Patent: Oct. 15, 1991

[54] COSMETIC PREPARATION CONTAINING CHITOSAN

[75] Inventors: Jean-Louis Leuba, Boussens; Harriet Link, Vevey; Peter Stoessel, Aarau; Jean-Louis Viret, Brent, all of Switzerland

[73] Assignee: Nestec S.A., Vevey, Switzerland

[21] Appl. No.: 428,882

[22] Filed: Oct. 30, 1989

[30] Foreign Application Priority Data

Nov. 28, 1988 [CH] Switzerland ............. 04418/88

[51] Int. Cl.$^5$ .............................. A61K 7/00
[52] U.S. Cl. ................. 514/844; 514/846; 514/847; 514/55; 536/20; 536/55.3
[58] Field of Search ............ 514/55, 844, 846, 847; 536/20, 55.3

[56] References Cited

U.S. PATENT DOCUMENTS

| | | | |
|---|---|---|---|
| 4,394,373 | 7/1983 | Malette et al. | 514/55 |
| 4,424,346 | 1/1984 | Hall et al. | 536/20 |
| 4,772,689 | 9/1988 | Lang et al. | 514/55 |
| 4,822,598 | 4/1989 | Lang et al. | 536/20 |
| 4,956,350 | 9/1990 | Mosbey | 514/55 |

FOREIGN PATENT DOCUMENTS

| | | |
|---|---|---|
| 2627419 | 6/1976 | Fed. Rep. of Germany . |
| 61-210014 | 9/1986 | Japan . |
| 62-83877 | 4/1987 | Japan . |

*Primary Examiner*—Ronald W. Griffin
*Assistant Examiner*—Everett White
*Attorney, Agent, or Firm*—Vogt & O'Donnell

[57] ABSTRACT

Chitosan in a form of a polymer having a molecular weight of from 3,000 to 700,000 is incorporated into a cosmetic preparation in an amount effective for inhibiting growth of microorganisms in the cosmetic preparation.

14 Claims, No Drawings

COSMETIC PREPARATION CONTAINING CHITOSAN

BACKGROUND OF THE INVENTION

This invention relates to cosmetic preparation containing chitosan.

The literature contains numerous examples of the use of chitosan.

Chitosan may be used in the treatment of burns. By immersion of the burnt body in a solution of chitosan acetate, a resistant oxygen-permeable film is formed over the surface of the wound and facilitates the healing process.

Chitosan in the form of a hydrochloride solution is also known to show high anti-infectious activity towards bacteria, as shown in JP 82.137930.

JP 87.083877 mentions the use of chitosan, preferably degraded by a chitonase, as a preservative in various products.

In the field of cosmetics, chitosan is known above all for its use in shampoos and capillary products for shaping and setting the hair, as in DE 26 27 419.

Chitosan can also be used to improve the cleansing and massaging properties of a compound applied to the skin, as described in JP 86.210014.

The cosmetic preparations generally keep fairly well in sterile packs. However, they are subjected to risks of contamination throughout their use.

When the container accommodating the preparation is opened, the microorganisms present in the ambient air can contaminate the preparation.

During the use of the preparation, the microorganisms on the surface of the skin can also contaminate the preparation. Such contamination can result in degradation of the preparation.

SUMMARY OF THE INVENTION

The object of the present invention is to overcome the disadvantages of the prior art and to provide a cosmetic preparation having good keeping properties which contains chitosan as preservative.

To this end, the chitosan according to the invention is selected from its polymers having a molecular weight in the range from 3,000 to 700,000.

One advantage of the invention is that a natural product is used as preservative.

Another advantage is that a plentiful and inexpensive product is used as preservative.

Another advantage is that only a small quantity of chitosan is introduced into the cosmetic preparation.

Another advantage lies in the use of a product to which microorganisms have no tolerance.

Another advantage lies in the provision of a cosmetic preparation which keeps for a long period in a sterile medium (sterile and hermetic pack) and in a non-sterile medium (non-hermetic pack or after opening)

DETAILED DESCRIPTION OF THE INVENTION

The chitosan used in accordance with the present invention is obtained by deacetylation of chitin with an alkali (sodium or potassium hydroxide, for example). Chitin is one of the most abundant biopolymers on earth. It is an important component of the exoskeleton of arthropodes, such as, for example, the cuticle of insects or the shell of crustaceans. Chitin is also a constituent element of the cell wall of certain moulds and yeasts.

It is assumed that the biological activity of chitosan is attributable to its polycationic nature. When they are protonated, the amine groups of chitosan interact with the electronegative sites situated at the surface of the cells of the microorganisms.

This interaction results in a modification of the permeability of the cell membrane which causes certain intracellular constituents or certain ions to be lost to the outside. This loss of intracellular substances is associated with inhibition of the growth of the microorganism. Other energy-generating mechanisms, such as respiration or fermentation, can also be disturbed and/or blocked by the addition of chitosan.

The chitosan used in accordance with the present invention may be of various origins. In particular, it may be the product of the deacetylation of chitin from crabs, shrimps or lobsters for example.

The physico-chemical properties and microstructure of the chitosan will depend upon the particular source selected and also on the various treatments applied, such as, for example, purification or deacetylation. The preferred chitosan according to the invention comes from chitin extracted from shrimps.

The degree of deacetylation of the chitin thereby forming the chitosan may have a certain bearing on its biological activity. This degree corresponds to the quantity of amine groups released so that the higher it is, the more effective the chitosan may be.

The degree of deacetylation of the chitosan according to the present invention is preferably from 70 to 95%.

It has been found that the chain length of the chitosan polymer can influence its behavior and bring about changes in its biological activity, in other words its ability to inhibit the growth of microorganisms.

It has been found in particular that, when the chitosan in the form of a polymer of small size (for example monomer, pentamer, heptamer), its biological activity is very low.

It is assumed that this is attributable to the fact that, because the chain of the polymer is too short, the local charge density is low and prevents the polymer from desirably interacting with the negative sites at the surface of the cell membrane. Accordingly, there is no significant change in the permeability of the membrane.

Chitosans of small size, i.e., low molecular weight, are not suitable as a preservative for the purposes of the invention.

By low molecular weight is meant a molecular weight below 3,000.

It has been found that chitosans of large size, i.e., of high molecular weight, also show low biological activity. It is assumed that this is attributable to a change in the molecular configuration of the chitosan. The chitosan may have a configuration varying from a simple, random coil to a more compact almost globular structure, this second structure probably being promoted in the case of high molecular weights.

The electrostatic interaction between the chitosan and the surface of the cells of the microorganisms could thus be limited due to the fact that the majority of active groups of the chitosan would be confined to the interior of the molecular structure and would be sterically inaccessible.

The chitosans of large size, i.e., high molecular weight, are not suitable as a preservative for the purposes of the invention. By high molecular weight is meant a molecular weight above 700,000.

The chitosan capable of inhibiting the growth of microorganisms according to the present invention thus has a molecular weight in the range from 3,000 to 700,000 and preferably in the range from 120,000 to 450,000.

Since the viscosity of a chitosan solution is dependent on its molecular weight, this value has proved to be suitable for characterizing a chitosan solution useable in accordance with the present invention. Thus, in one preferred use of the chitosan in accordance with the invention as a preservative in a cosmetic preparation, the chitosan is incorporated in the cosmetic preparation in the form of an aqueous solution having a viscosity of from 1 to 80 mPa.s for a chitosan concentration of 1%. The molecular weight of the chitosan and the viscosity of the chitosan solutions are measured by the methods described hereinafter prior to the Examples.

The chitosan content of the cosmetic preparation can influence the biological activity of the chitosan.

An excessively high content can induce repulsion phenomena between chitosan polymers and prevent them approaching the cell membrane.

An excessively low content is unable to afford the preparation adequate protection against microbial contamination.

The cosmetic preparation according to the invention may have a chitosan content of from 50 to 5,000 $\mu g/g$ and preferably from 100 to 300 $\mu g/g$.

The biological activity of the chitosan may also be governed by its solubility. The chitosan incorporated in a cosmetic preparation in the form of a powder in aqueous suspension may be less active than a solution.

The solubility of the chitosan may be improved by ultrasonication of a chitosan dispersion and/or by freeze-drying after centrifugation. Ultrasonication can be an excellent method of cleaving the polymer chains to make them more soluble. This produces a rearrangement of the microstructure of chitosan which enables it solubility and even its biological activity to be increased. This activity may be doubled or even multiplied by a factor of 8 where ultrasonicated and/or freeze-dried chitosan is used.

In addition, to be biologically active, the chitosan must preferably be in its polycationic form, i.e., at a pH below its pKa which is 6.2.

To ensure a high positive charge density, the chitosan solutions will preferably have a pH value in the range from 5.0 to 5.5.

The chitosan may be incorporated in any cosmetic preparation, such as a milk, a lotion, a cream or a gel. It is merely preferable that the cosmetic preparation have a low anion content.

TESTS AND EXAMPLES

A certain number of microorganisms are used to test the biological activity of the various chitosans.

These microorganisms are selected from those capable of damaging the health of the users or from those capable of producing a deterioration in the cosmetic preparation. The following have been selected from the numerous microorganisms which comply with these criteria:
gram-negative bacteria (*Escherichia coli* and *Pseudomonas aeruginosa*),
gram-positive bacteria (*Staphylococcus aureus*, *Streptococcus faecalis* and *Bacillus cereus*) and
yeasts (*Candida albicans*).

MEASURING METHODS

Viscosity

Viscosity is measured on solutions of 1% chitosan and 1% acetic acid which are left standing for 2 weeks for the viscosity to stabilize.

The measurement is carried out using a Bohlin VOR rheometer under the following conditions:
measuring system: C. 14 cylinder
tension bar: 0.24 g.cm and 19.8 g.cm
initial dwell time: 60 s
measuring time: 20 s at constant deformation
integration time: 10 s
temperature: 20° C.
shear rate 11.64 $s^{-1}$

MOLECULAR WEIGHT

Molecular weight is measured by laser light-scattering using the method of R.A. Muzzarelli, C. Lough and M. Emanuelli described in the article "The Molecular Weight of Chitosans studied by Laser Light-Scattering", published in Carbohydrate Res. 164, 433–442 (1987).

MICROORGANISM GROWTH

The number of germs may be determined by two methods: by counting or by spectrophotometry.

(1) Counting

A 1 ml sample is taken from the medium to be analyzed and diluted with 9 ml of a physiological salt solution. This solution is diluted in a ratio of 10:10, after which 1 ml of the diluted solution is placed on a Petri plate and mixed with 10 ml nutrient agar. The plate is then left to incubate overnight at 37° C., after which the number of germs which have developed is counted.

(2) Spectrophotometry

Since the preceding method has the disadvantage of being slow, it is easier to measure the number of germs in suspension by spectrophotometry. A suspension of germs transmits the light passing through it differently from a control suspension containing no germs.

The light transmitted is measured by spectrophotometry for each solution and the reduction in transmission enables the number of germs in suspension to be determined.

This measurement is carried out with a spectrophotometer at a wavelength of 550 nm.

However, this method is not very sensitive and only enables a number of germs larger than or equal to $10^6$ germs per ml to be detected.

(3) *C. albicans*

So far as this yeast is concerned, the technique of microscopic counting is applied using a Neubauer cell.

The invention is illustrated by the following tests and examples, the tests illustrating the "in vitro" biological activity of the various samples of chitosan. The percentages are by weight except for the degree of deacetylation.

BIOLOGICAL ACTIVITY TESTS

PREPARATION OF CHITOSAN SAMPLES

Various chitosan samples are prepared as follows in the form of aqueous culture media of microorganisms containing chitosan in solution:

for the bacteria, an aqueous CAYE medium containing 1% hydrolyzed casein, 0.5% yeast extract and 0.2% glucose is prepared for the yeast, an aqueous YES medium containing 0.5% yeast extract and 2% sucrose is prepared the medium is acidified to pH 2 by addition of 1 N hydrochloric acid various chitosans of various origins all having a degree of deacetylation of from 80 to 95% are dissolved solved in a 1% hydrochloric acid solution to obtain a chitosan concentration of 1% the culture medium is divided into several batches to which the chitosan is added with stirring the pH of each batch is adjusted to 5.8 by addition of 1 N sodium hydroxide and the final volume is adjusted with distilled water the various batches are sterilized in an autoclave for 15 minutes at 121° C.

The control samples only contain the culture media of which the pH has been adjusted to 5.8.

The various chitosans tested are listed in the following Table in the order of increasing molecular weight and viscosity:

| Sample | Molecular weight | Viscosity (mPa.s) |
|---|---|---|
| 1 | 127,925 | 7.85 |
| 2 | 135,190 | 7.59 |
| 3 | 166,430 | 13.69 |
| 4 | 193,610 | 53.02 |
| 5 | 233,600 | 50.22 |
| 6 | 254,050 | 27.69 |
| 7 | 318,890 | 51.48 |
| 8 | 351,460 | 64.03 |
| 9 | 356,400 | 51.85 |
| 10 | 437,710 | 69.99 |
| 11 | 781,960 | 82.82 |
| 12 | 993,530 | 120.0 |
| 13 | 1,140,000 | 172.7 |

PREPARATION OF MICROORGANISM CULTURES

The bacteria are cultured for 8 h on a nutrient medium (in fusion based on veal treated with agar) and then for 16 h on a CAYE medium at pH 5.8.

The yeast is cultured for 3 days on a YES medium at pH 5.8.

The culture is then diluted so that 1 ml culture contains approximately $10^7$ germs.

TEST NO. 1

The various chitosan samples, of which the concentration of 50 μg chitosan per ml culture medium, are inoculated with a suspension of germs of "Candida albicans" to obtain an initial number of approximately $10^5$ germs per ml.

The samples are incubated by agitation at 110 r.p.m. at 23° C.

The number of germs in each sample is measured daily.

An inhibition of growth of "C. albicans" due to the chitosan is observed. The time interval between the day the C. albicans is inoculated and the day when the number of germs of C. albicans begins to grown again is measured.

The following results are obtained (T =control):

| Sample | T | 1 | 2 | 3 | 4 | 5 | 6 | 7 | 8 | 9 | 10 | 11 | 12 | 13 |
|---|---|---|---|---|---|---|---|---|---|---|---|---|---|---|
| Time interval (days) | 0 | 28 | 18 | 25 | 14 | 14 | 13 | 12 | 12 | 15 | 23 | 3 | 5 | 3 |
| | | | | | | | | | | | | comparison | | |

It can be seen that the addition of the chitosan samples 1-10 enables the resumption of growth of the number of germs to be retarded for a period of at least 12 days.

TEST NO. 2

Various chitosan samples, of which the concentration is 100 μg chitosan per ml culture medium, are inoculated with suspensions of different organisms at a rate of 1 microorganism per sample to obtain an initial number of approximately $10^5$ germs per ml.

The samples are left to incubate at 37° C. (43° C. for "Ps. aeruginosa") and the effect of the chitosan on the resumption of growth of the bacteria is recorded by measuring the number of germs by spectrophotometry at regular intervals.

By way of illustration, the following Table shows the evolution of the percentage transmission as a function of time for the bacterium "Staph. aureus" for four chitosan samples.

The precentage transmission is inversely proportional to the number of germs in solution (0 signifying that the light is transmitted with difficulty in view of the very large number of germs present).

| Sample | % transmission | | | | | |
|---|---|---|---|---|---|---|
| | 0 h | 6 h | 8 h | 24 h | 48 h | 120 h |
| 2 | 70 | 70 | 80 | 91 | 93 | 7 |
| 4 | 46 | 46 | 46 | 46 | 63 | 7 |
| 5 | 61 | 68 | 68 | 74 | 64 | 7 |
| 9 | 91 | 91 | 91 | 91 | 82 | 7 |
| Control | 100 | 70 | 25 | 7 | 7 | 7 |

The initial percentage transmission differs according to the samples tested. This is due to the appearance of slight turbidity in the solution attributable to interaction between the chitosan and the culture medium.

However, since this turbidity remains constant as a function of time, it does not influence the general trend of the evolution curves.

For each bacterium tested, the chitosan samples are classified according to the duration of their inhibiting power:

| | Staph. aureus |
|---|---|
| . at least 8 h: | 1 |
| . at least 24 h: | 3-6-7-8-10 |
| . at least 48 h: | 2-4-5-9 |
| | Strep. faecalis |
| . at least 6 h: | 11-12 (comparison) |
| . at least 8 h: | 3-7-10 |
| - at least 48 h: | 2-4-5-6-8-9 |
| | B. cereus |
| . at least 24 h: | 6-7-8 |
| . at least 96 h: | 1-2-3-4-5-9-10 |
| | E. coli |
| . at least 6 h: | 9 |

-continued

| | |
|---|---|
| . at least 8 h: | 2-4 |
| | *Ps. aeruginosa* |
| . at least 10 h: | 3-4-10 |
| . at least 14 h: | 2-5-9 |

It may be concluded from this test that the tested chitosans samples 1-10 considerably inhibit the growth of the bacteria.

TEST NO. 3

The procedure is similar to that described for test No. 2 except for the fact that chitosan samples in which the chitosan concentration is 200 μm per ml culture medium are used and the number of germs is determined by counting.

The following Tables show the evolution of the number of germs per ml as a function of time for various chitosan samples and for various microorganisms.

*Streptococcus faecalis*
Initially: $2.6 \cdot 10^6$ germs per ml

| Sample (molecular weight) | Number of germs per ml | | | | |
|---|---|---|---|---|---|
| | 4 h | 8 h | 24 h | 48 h | 144 h |
| 1 (128,000) | $3.1 \cdot 10^4$ | 2200 | $10^6$ | $>10^7$ | $5.6 \cdot 10^6$ |
| 2 (135,000) | 1800 | $4.6 \cdot 10^4$ | $2 \cdot 10^4$ | $66 \cdot 10^4$ | $5.6 \cdot 10^6$ |
| 3 (166,000) | 93 | 26 | 120 | 290 | $5.5 \cdot 10^6$ |
| 8 (351,000) | 20 | 50 | $1.4 \cdot 10^6$ | $>10^7$ | $58 \cdot 10^4$ |
| Control | $45 \cdot 10^6$ | $2 \cdot 10^8$ | $2.8 \cdot 10^8$ | ND | ND |

*Staphylococcus aureus*
Initially: $8.1 \cdot 10^6$ germs per ml

| Sample (molecular weight) | Number of germs per ml | | | | |
|---|---|---|---|---|---|
| | 4 h | 8 h | 24 h | 48 h | 72 h | 168 h |
| 1 (128,000) | 6200 | 3100 | $55 \cdot 10^4$ | $12 \cdot 10^4$ | $49 \cdot 10^4$ | $>10^7$ |
| 2 (135,000) | 400 | 43 | $28 \cdot 10^4$ | $2.4 \cdot 10^6$ | $3.6 \cdot 10^6$ | $>10^7$ |
| 3 (166,000) | $12 \cdot 10^4$ | 2 | $5.8 \cdot 10^4$ | $12 \cdot 10^4$ | $10^5$ | 6300 |
| 8 (351,000) | 100 | 100 | $16 \cdot 10^4$ | $17 \cdot 10^4$ | $5.7 \cdot 10^4$ | $9.2 \cdot 10^4$ |
| Control | $17 \cdot 10^6$ | $58 \cdot 10^6$ | $10^8$ | ND | ND | ND |

*Bacillus cereus*
Initially: $9.1 \cdot 10^5$ germs per ml

| Sample (molecular weight) | Number of germs per ml | | | | |
|---|---|---|---|---|---|
| | 4 h | 8 h | 24 h | 48 h | 120 h |
| 1 (128,000) | 7 | 4 | 0 | 0 | 0 |
| 2 (135,000) | 0 | 0 | $39 \cdot 10^4$ | $1.3 \cdot 10^6$ | $2.1 \cdot 10^4$ |
| 3 (166,000) | 8 | 2 | 1 | 0 | 0 |
| 8 (351,000) | 1 | 0 | 0 | 0 | $1.2 \cdot 10^6$ |
| Control | $11 \cdot 10^6$ | $3 \cdot 10^7$ | $4 \cdot 10^6$ | ND | ND |

*Pseudomonas aeruginosa*
Initially: $8.1 \cdot 10^6$ germs per ml

| Sample (molecular weight) | Number of germs per ml | | | |
|---|---|---|---|---|
| | 4 h | 8 h | 24 h | 48 h |
| 1 (128,000) | $27 \cdot 10^4$ | $1.2 \cdot 10^6$ | $>10^7$ | ND |
| 2 (135,000) | 6200 | 1600 | 9800 | $2.1 \cdot 10^6$ |
| 3 (166,000) | 7300 | 3400 | $7.7 \cdot 10^4$ | $>10^7$ |
| 8 (351,000) | $34 \cdot 10^4$ | $63 \cdot 10^4$ | $>10^7$ | ND |
| Control | $19 \cdot 10^6$ | $36 \cdot 10^6$ | $10^9$ | ND |

*E. coli*
Initially: $1.6 \cdot 10^5$ germs per ml

| Sample (molecular weight) | Number of germs per ml | | |
|---|---|---|---|
| | 4 h | 8 h | 24 h |
| 1 (128,000) | 6600 | $1.2 \cdot 10^6$ | $>10^8$ |

-continued

| | | | |
|---|---|---|---|
| 2 (135,000) | $1.8 \cdot 10^4$ | $>10^7$ | $>10^8$ |
| 3 (166,000) | 6400 | $1.2 \cdot 10^6$ | $>10^8$ |
| 8 (351,000) | $36 \cdot 10^4$ | $>10^7$ | $>10^8$ |
| Control | $6.3 \cdot 10^6$ | $4 \cdot 10^8$ | $2 \cdot 10^9$ |

ND = non-determinable

During the first 4 or even 8 hours of incubation, the number of germs present in the samples containing chitosan decreases significantly.

This number then tends to reassume and even exceed its initial value. This shows that the samples containing chitosan show bacteriostatic activity towards the microorganisms tested over periods ranging from 4 hours (E. coli) to 48 hours (St. faecalis and St. aureus).

It can also be seen that samples 1 and 3 show bactericidal activity towards the bacterium B. cereus.

These three tests clearly show that samples of chitosan having a molecular weight in the range from 3,000 to 700,000 show bacteriostatic and even bactericidal activity towards microorganisms.

TEST NO. 4

Several samples varying in concentration from 50 µg to 5,000 µg chitosan per ml medium are prepared from chitosan having a molecular weight of approximately 128,000.

These samples are inoculated with a suspension of "C. albicans" to obtain an initial number of approximately $10^5$ germs per ml, after which each sample is distributed in several sterile glass tubes which are then hermetically sealed.

The samples are left to incubate in darkness at 23° C. for a period of 6 months. One tube for each concentration is opened at regular time intervals and the number of germs present is measured.

A period is obtained for each concentration, during which the chitosan is active and inhibits the growth of the germs present.

For the samples containing 250 µg and more of chitosan per ml, germ growth is inhibited for a minimum period of 6 months because no germ growth is detected in these tubes.

For the sample containing 50 µg chitosan per ml, germ growth is inhibited for 5 weeks and then resumes.

For comparison, a sample containing 20 µg chitosan per ml inhibits germ growth for only 1 day.

The chitosan can thus remain active for long periods if it is present in a sufficient concentration.

TEST NO. 5 (COMPARISON TEST)

To study the activity of chitosans of low molecular weight, 5 g chitosan is partially hydrolyzed with concentrated HCl for 21 h at 53° C.

The resulting chitosan is dried in vacuo at 30° C. and the various oligomers are separated on an ion exchange resin (AG 50 W −X 8), the eluent used being hydrochloric acid in a concentration varying from to 5.5 N. The various eluate fractions are separated by gel filtration (Fractogel TSK HW −40), the eluant used being a 0.2% formic acid solution. The various oligomers are identified by thin-layer chromatography.

The antimicrobial activity of the pentamer and heptamer of glucosamine is tested by the method described in test No. 4 using the yeast C. albicans for various concentrations of chitosan.

No inhibition of the growth of the yeast is observed for a chitosan concentration of 1 mg per ml culture medium (i.e. 1,000 µg/g).

EXAMPLE 1

10 mg chitosan from shrimps having a molecular weight of approximately 180,000 and a degree of deacetylation of approximately 85% are dispersed in 600 ml distilled water. 30 ml acetic acid are then added and the whole is dissolved by stirring. The pH is adjusted to 5.8 by addition of sodium hydroxide and the volume of the solution is adjusted to 1 liter by addition of distilled water.

Four batches of toilet milk are prepared at the same time, containing 6% $C_{12-18}$ alkyl ester of polyethylene glycol, 5% glycerol stearate, 3% isodecyl laurate, 3% $C^{10-18}$ fatty acid triglycerides, 1% cetyl alcohol, 0.8% dimethicone (silicone oil), 0.4% hydroxyethyl cellulose, 3% sorbitol (70%) and 0.2% perfume.

One batch is kept as control and a few ml of chitosan solution are added to each of the other three batches so that batches having respective chitosan contents of 0, 50, 100 and 200 µg/g are obtained.

The pH is adjusted to 6 and the balance to 100% is made up with distilled water.

The batches are inoculated with a suspension of microorganisms to obtain an initial number of approximately $10^4$ germs per ml.

The batches are stored at ambient temperature and in the absence of light. The number of germs present in the toilet milk are measured at different stages of evolution: after inoculation, after 1 week, after 2 weeks, after 3 weeks and after 4 weeks.

The microorganisms selected are:
I. "E. coli"
II. "Ps. aeruginosa"
III. "Staph. aureus"
IV. "Strep. faecalis"
V. "C. albicans"

The results obtained are shown in the following Table:

| Microorganisms | I | II | III | IV | V |
|---|---|---|---|---|---|
| After inoculation | | | | | |
| Batch A (control) | $34 \cdot 10^3$ | $8 \cdot 10^4$ | $42 \cdot 10^4$ | $7 \cdot 10^4$ | $36 \cdot 10^5$ |
| Batch B (50 µg/g) | $35 \cdot 10^3$ | 10 | $18 \cdot 10^3$ | $7 \cdot 10^4$ | $9 \cdot 10^3$ |
| Batch C (100 µg/g) | $29 \cdot 10^3$ | 10 | $6 \cdot 10^4$ | $53 \cdot 10^3$ | $9 \cdot 10^3$ |
| Batch D (200 µg/g) | $24 \cdot 10^3$ | 10 | $27 \cdot 10^3$ | $24 \cdot 10^3$ | 80 |
| After 1 week | | | | | |
| Batch A | $3 \cdot 10^7$ | $16 \cdot 10^5$ | $10^4$ | 3500 | $3 \cdot 10^6$ |
| Batch B | 10 | 10 | 10 | 10 | 10 |
| Batch C | 10 | 10 | 10 | 10 | 10 |
| Batch D | 10 | 10 | 10 | 10 | 10 |
| After 2 weeks | | | | | |
| Batch A | $13 \cdot 10^6$ | $10^6$ | 500 | 20 | $10^6$ |
| Batch B | — | — | — | — | 10 |
| Batch C | — | — | — | — | 10 |

| Microorganisms | I | II | III | IV | V |
|---|---|---|---|---|---|
| Batch D | — | — | — | — | 10 |
| After 3 weeks | | | | | |
| Batch A | $6 \cdot 10^6$ | $48 \cdot 10^5$ | 60 | 50 | $8 \cdot 10^6$ |
| Batch B | — | — | — | — | 10 |
| Batch C | — | — | — | — | 10 |
| Batch D | — | — | — | — | 10 |
| After 4 weeks | | | | | |
| Batch A | $5 \cdot 10^6$ | $10^7$ | 50 | 10 | $9 \cdot 10^6$ |
| Batch B | — | — | — | — | 10 |
| Batch C | — | — | — | — | 10 |
| Batch D | — | — | — | — | 10 |

It can be seen that all the milks containing chitosan inhibit the growth of the bacteria or yeasts which they contain. The effect is visible from the first week.

The bacteriostatic or even bactericidal activity of the chitosan is distinct, even in regard to the milks of low chitosan content (50 µg/g).

EXAMPLE 2

A cosmetic cream containing chitosan is prepared as follows:
- 77 ml of a buffer solution at pH =5.7 (based on sodium phosphate) are prepared,
- 10 mg chitosan from shrimps dissolved in dilute acetic acid and having a molecular weight of approximately 180,000 and a degree of deacetylation of approximately 85% are added,
- 8 g glycerol are then added, after which the mixture is heated on a water bath 80° C.
- at the same time, 15 g glycerol stearate are melted at 80° C. and slowly added with stirring to the above mixture,
- the mixture is left to cool to ambient temperature with occasional homogenization.

A cream containing 100 µg/g chitosan is obtained. A cream containing 250 µg/g chitosan is prepared in the same way.

Control creams with no chitosan added are also prepared.

The various creams are placed in non-sterilized pots and stored in darkness at ambient temperature. Signs of contamination appear in the control after 2 months. Microscopic examination reveals the gradual appearance of fungal spores and hyphae.

The creams containing chitosan show no trace of contamination, even after 1 year.

We claim:

1. A composition comprising a cosmetic preparation and chitosan contained therein wherein the chitosan is in the form of a polymer having a molecular weight of from 120,000 to 450,000 and is contained in the preparation in the amount of from 50 µg chitosan/g of the preparation to 5000 µg chitosan/g of the preparation.

2. A composition according to claim 1 wherein the chitosan is the product of the deacetylation of chitin deacetylated to a degree of from 70% to 95%.

3. A composition according to claim 1 wherein the preparation contains the chitosan in an amount of from 100 µg/g to 300 µg/g.

4. A composition according to claim 1 wherein the chitosan is in polycationic form.

5. A process for preserving a cosmetic preparation in comprising incorporating chitosan in the form of a polymer having a molecular weight of from 120,000 to 450,000 into a cosmetic preparation in an amount of from 50 µg chitosan/g of the preparation of 5000 µg chitosan/g of the preparation for inhibiting growth of microorganisms in the cosmetic preparation.

6. A process according to claim 5 wherein the chitosan incorporated into the preparation is in aqueous solution.

7. A process according to claim 6 wherein the aqueous solution has a pH below 6.2.

8. A process according to claim 7 wherein the aqueous solution has a pH of from 5.0 to 5.5.

9. A process according to claim 6 wherein the aqueous solution has a viscosity of from 1 mPa to 80 mPa for a chitosan concentration of 1%.

10. A process according to claim 5 wherein the chitosan incorporated into the preparation is a powder in aqueous suspension.

11. A process according to claim 5 wherein the chitosan incorporated into the preparation has been subjected to dispersion in water and ultrasonification.

12. A process according to claim 11 wherein the chitosan incorporated into the preparation also has been subjected to freeze drying.

13. A process according to claim 5 wherein the chitosan incorporated into the preparation has been subjected to freeze drying.

14. A process according to claim 5 wherein the preparation contains the chitosan in an amount of from 100 µg/g to 300 µg/g.

* * * * *

UNITED STATES PATENT AND TRADEMARK OFFICE
CERTIFICATE OF CORRECTION

PATENT NO. : 5,057,542

DATED : October 15, 1991

INVENTOR(S) : Jean-Louis LEUBA, et al.

It is certified that error appears in the above-identified patent and that said Letters Patent is hereby corrected as shown below:

Column 2, line 31, after " deacetylation of" insert --the chitin thereby forming--.

Column 12, line 8 (line 5 of claim 1), "the " should be --an--.

Column 12, line 18 (line 1 of claim 5), after "preparation" delete "in".

Column 12, line 19 (line 2 of claim 5), "the" should be --a--.

Signed and Sealed this

Nineteenth Day of January, 1993

Attest:

DOUGLAS B. COMER

*Attesting Officer*     Acting Commissioner of Patents and Trademarks